United States Patent [19]

Helling et al.

[11] Patent Number: 4,751,434
[45] Date of Patent: Jun. 14, 1988

[54] SELF-ILLUMINATED SEALED COOL LIGHT DISPLAY AND METHOD

[76] Inventors: James C. Helling, 4810 Park Newport Dr., Newport Beach, Calif. 92660; Anders V. Beckrot, 615 High Dr., Laguna Beach, Calif. 92651

[21] Appl. No.: 891,263

[22] Filed: Jul. 28, 1986

[51] Int. Cl.⁴ .................... H05B 37/00; H05B 39/00; H05B 41/00
[52] U.S. Cl. .................. 315/183; 40/152.1; 40/152.2; 315/248; 315/DIG. 7
[58] Field of Search ............. 40/152.1, 152.2; 315/182, 183, 112, 113, 248, DIG. 7

[56] References Cited

U.S. PATENT DOCUMENTS

| | | | |
|---|---|---|---|
| 2,500,511 | 3/1950 | Bonnet | 40/152.2 X |
| 2,731,585 | 1/1956 | Rousseau | 40/152.2 |
| 2,877,384 | 3/1959 | Gould | 40/152.2 X |
| 3,783,544 | 1/1974 | Brody | 40/152.2 |
| 4,059,916 | 11/1977 | Tachihara et al. | 40/152.2 |
| 4,282,669 | 8/1981 | Riedmont | 40/152.2 |
| 4,386,476 | 6/1983 | Schulman | 40/152.2 |
| 4,507,884 | 4/1985 | Kazanjian | 40/152.2 |

Primary Examiner—Saxfield Chatmon
Attorney, Agent, or Firm—Wilfred G. Caldwell

[57] ABSTRACT

The invention comprises a fluid-tight light box containing a cold cathode light source activated by a high frequency ballast circuit small enough to be contained in the box.

At least the box bottom interior is coated with a crinkle or matte finish to cause uniform brightness at or adjacent to a window in the upper side of the box. The ballast circuit is preferably also coated to avoid shadow effects.

A milky element may comprise the window or be positioned adjacent thereto to comprise a light diffuser for a transparency adjacent thereto or the transparency may be coated on its reverse side with a diffuser coating.

This display or portrait exhibitor may measure less than 2 inches thick and this is the reason the light reflective path and materials are so critical.

10 Claims, 8 Drawing Sheets

SELF-ILLUMINATED SEALED COOL LIGHT DISPLAY AND METHOD

BACKGROUND OF THE INVENTION

1. Field of the Invention

The invention relates, in general, to a lighted pictorial display or advertising attractive.

2. Description of the Prior Art

In the past, cool light displays required ballasts which were several inches thick and weighed to 14 pounds. Heating problems prevented the sealing of such lighted displays, and dust, water vapor and other pollutants entered the case and stuck to the hotter components, thus, emasculating the pictorial presentation and cluttering the casing or housing. The necessary air circulation, for cooling purposes, simply multiplied the problems of air-borne particles. Outdoor use also complicated the wiring system, and the display features through hostile water vapors, corrosion and rust problems.

Miniaturization of such attractives was quite impossible because of such adversities, and also, because structures and materials capable of uniform brilliance in thin displays are unknown; as necessitated by short gap light reflection. Also, high voltages in confined regions, under heavy power requirements, introduced problems of shorts, transformer hum and insulation.

The present invention overcomes each of these problems, while introducing a much improved cool light sealed display, which may include a small high frequency ballast circuit, suitable for hanging on interior walls or on exterior supporting structures.

SUMMARY OF THE INVENTION

The invention comprises a novel light display structure and method wherein a housing, in the form of a plastic and/or partly extruded box, or the like, is provided which has a depth of 2 inches, or less. A plastic or glass window pane closes the top of the box, and a cold cathode lighting source (preferably a neon tube) is supported within the box from the plastic bottom thereof. A transparency is supported adjacent to the window for viewing there through. It is a photographic negative, blown up from family negatives commercial photos, scenery, drawings, or full-size originals including portraits to comprise the image. Either the transparency has a diffusing coating on the reverse or lower side thereof or a diffuser element is supported adjacent the rear surface of the image element. The image or image and diffuser may slide into and out of the box for facilitating different views. A power supply component (i.e.) an high frequency ballast circuit may be included within the box for supplying low current, high frequency energy to the lighting source. It is operable from a 24 volt power supply main to insure safety and convenience. The interior of the bottom of the box is coated with a crinkle or matte finish in order that the transparency is illuminated uniformly by both direct and reflected light across such a small air gap.

DESCRIPTION OF A PREFERRED EMBODIMENT

Figure 1:
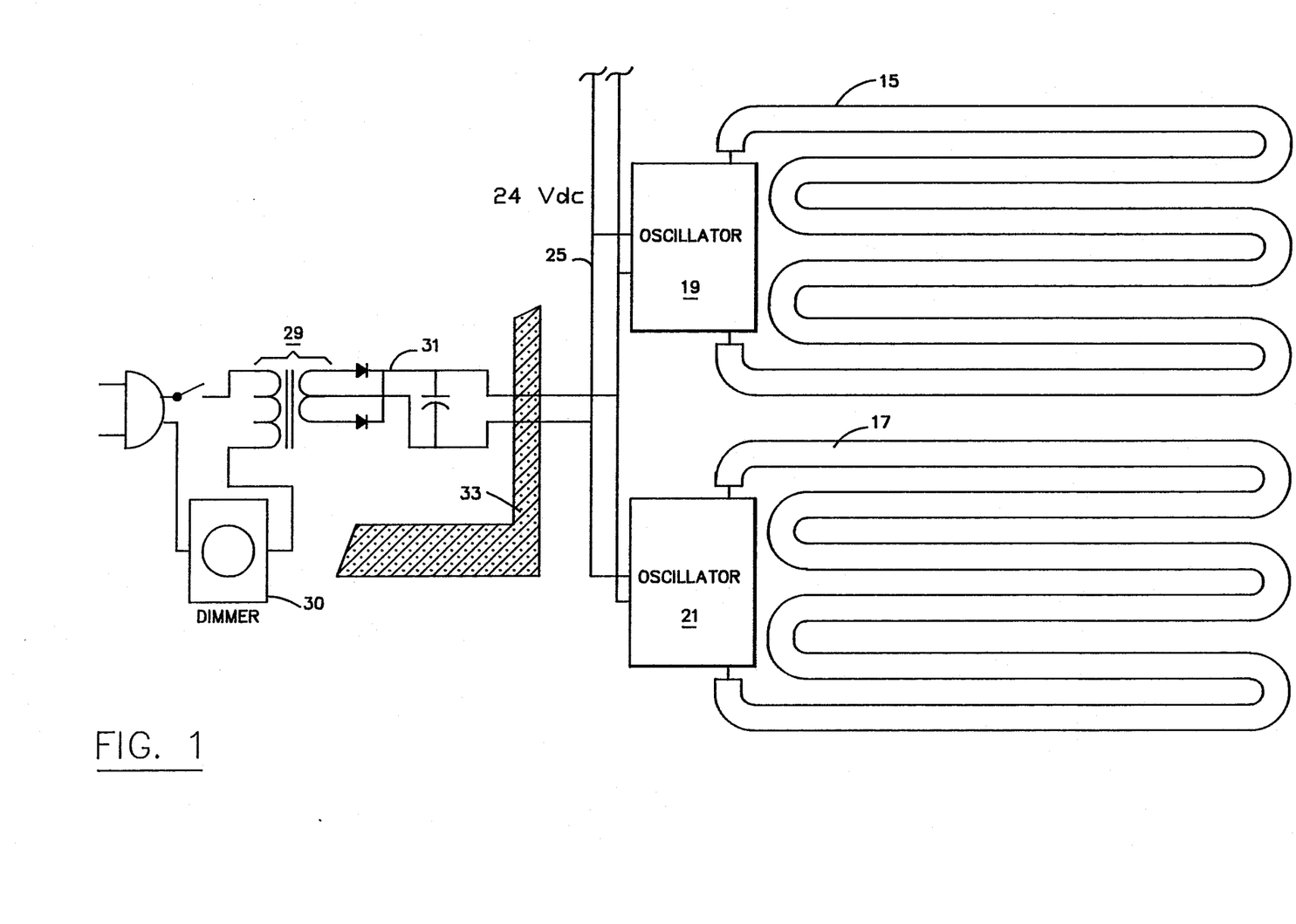
FIG. 1 is a schematic view of multiple lighting sources supplied from a single 24 volt DC power source.

In FIG. 1, a pair of configured neon bulbs 15, 17 is shown in plan view. Each bulb may (e.g.) have a length of 16 feet and a diameter of 12 mm., for illumination by a 25 kilohertz, 3000 volt source with operating current of 20 m.a.

The high frequency ballast circuit 19 and 21 are capable of this type operation, each serving as a high frequency supply operated from 24 volt dc main 25 supplied by a power supply or TR set 27.

These power supplies including the high frequency ballast circuit are fully described in U.S. patent application entitled, High Frequency Ballast Circuit, filed on July 28, 1986 by Dale Folwell, et al, now U.S. Pat. No. 4,700,111.

They may incorporate the rectifier of the TR sets 27 within a common housing or provide separate transformers, per se or TR sets, as in FIG. 1. The TR sets may be purchased off-the-shelf and simply comprise the transformer 29 and rectifier 31, here shown behind wall 33.

A typical high frequency ballast circuit 19 may be contained in a housing measuring approximately 1½ inch high by 2 inches wide by 5.9 inches long and weighing less than a pound, thereby permitting incorporation of the high frequency ballast circuit behind or border portion of a picture, within the picture frame, or directly behind the image in the lighted box housing thereof.

In FIG. 1, the neon tubes 15 and 17 may each measure 16 feet in length, being configured to conform to the size of a wall picture, such as 30 inches in height by 24 inches in width. With the high frequency ballast circuit incorporated into the picture, the depth may be less than 2 inches and except for the self-illumination feature, the picture may generally resemble other on the same wall, of conventional nature.

The neon bulbs are commercially available and offer the very useful advantage of long life, perhaps 20 years, for use in a closed non-cooled, arrangement.

Figure 2:
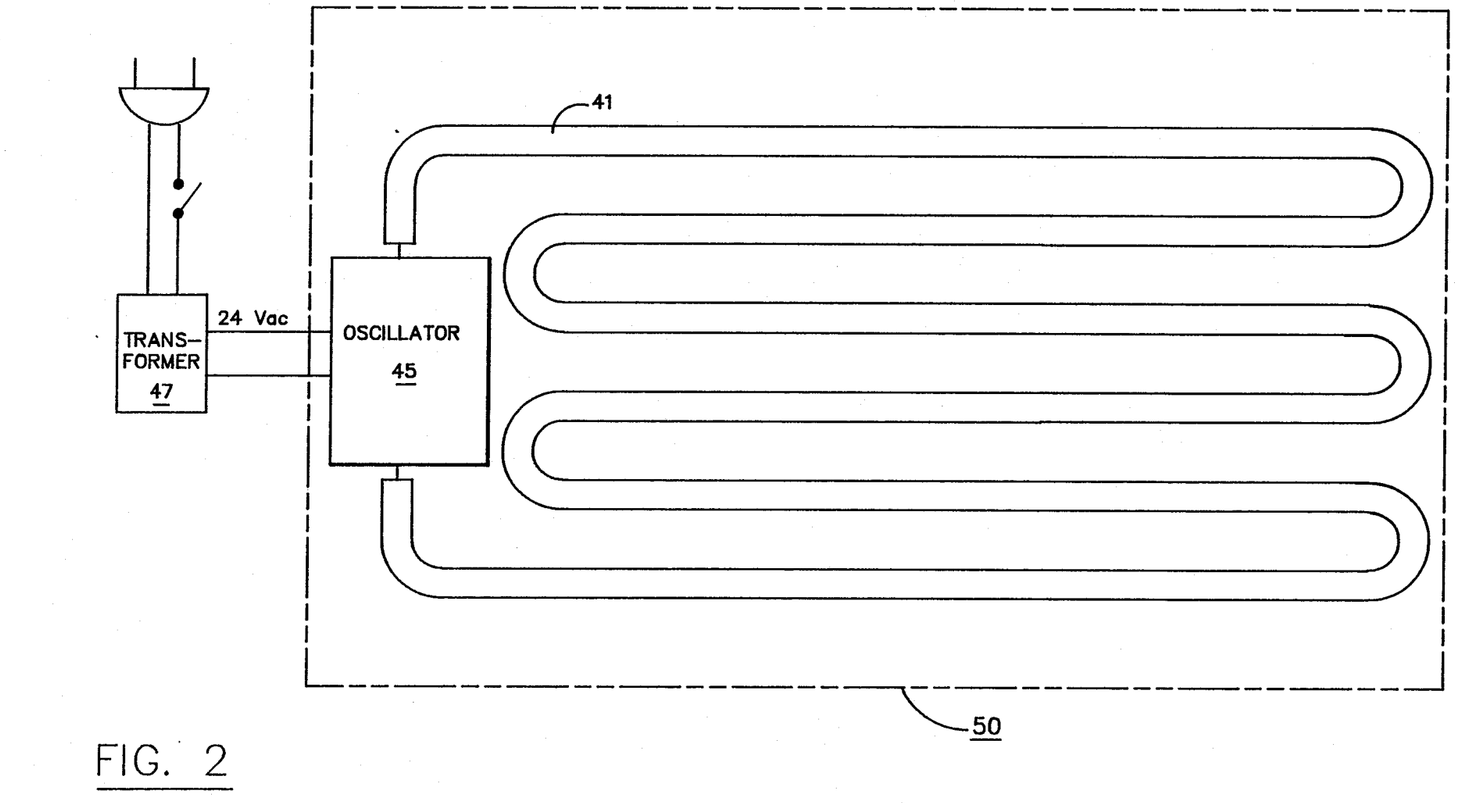
FIG. 2 shows a single lighting source supplied by a 24 volt AC source.

In FIG. 2, a single neon bulb 41 is powered from high frequency ballast circuit 45, in turn, remotely powered from remote transformer 47 by 24 volts ac.

Thus, in either configuration of FIG. 1 or FIG. 2, only 24 volts is used in the product, be it a picture or display, indoors or outdoors and, accordingly, it is unnecessary to obtain UL Approved for any of the numerous available products.

Figure 3:
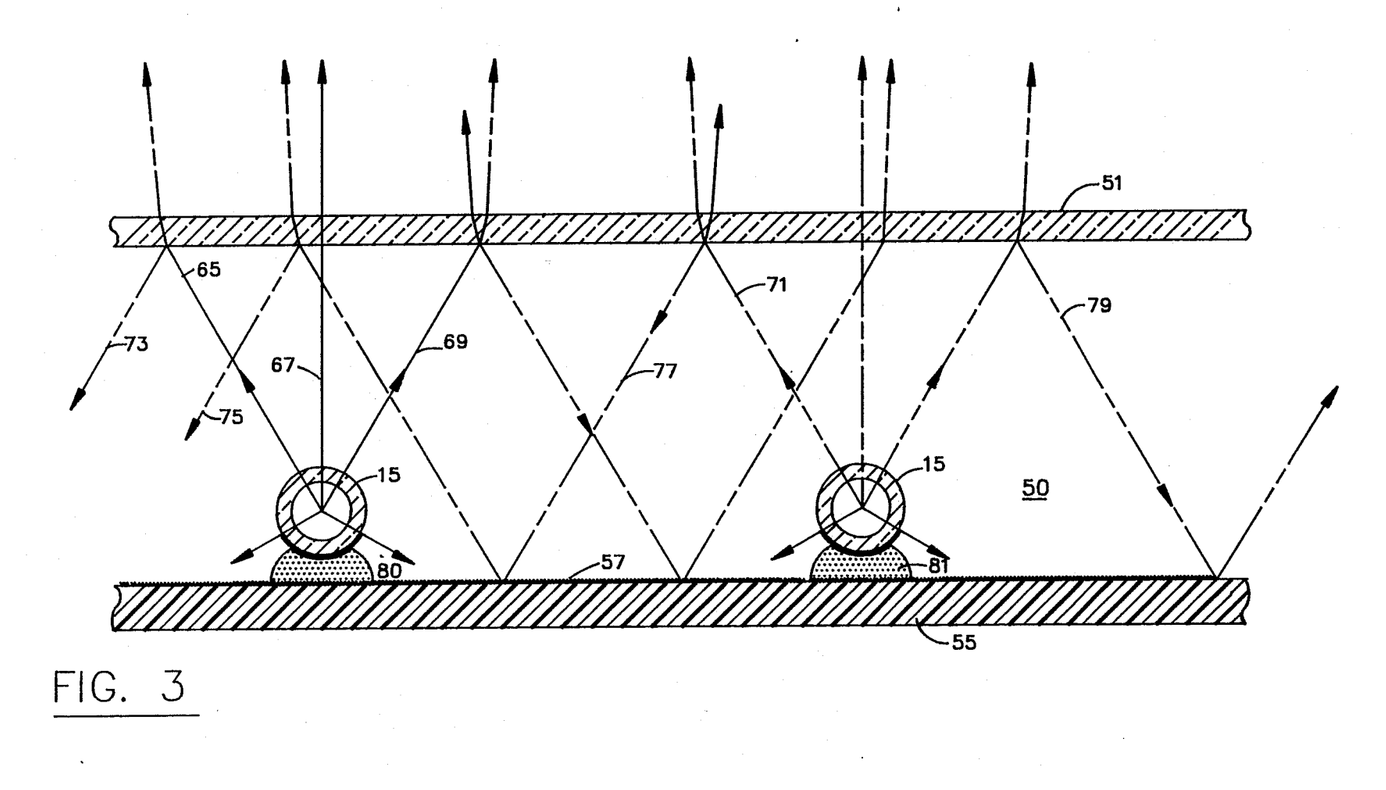
FIG. 3 is a sectional view through a rectangular box housing showing the cold cathode lighting source, transparency support, with light indicated by arrows being reflected from the matte interior coating.
Figures 6, 6A:
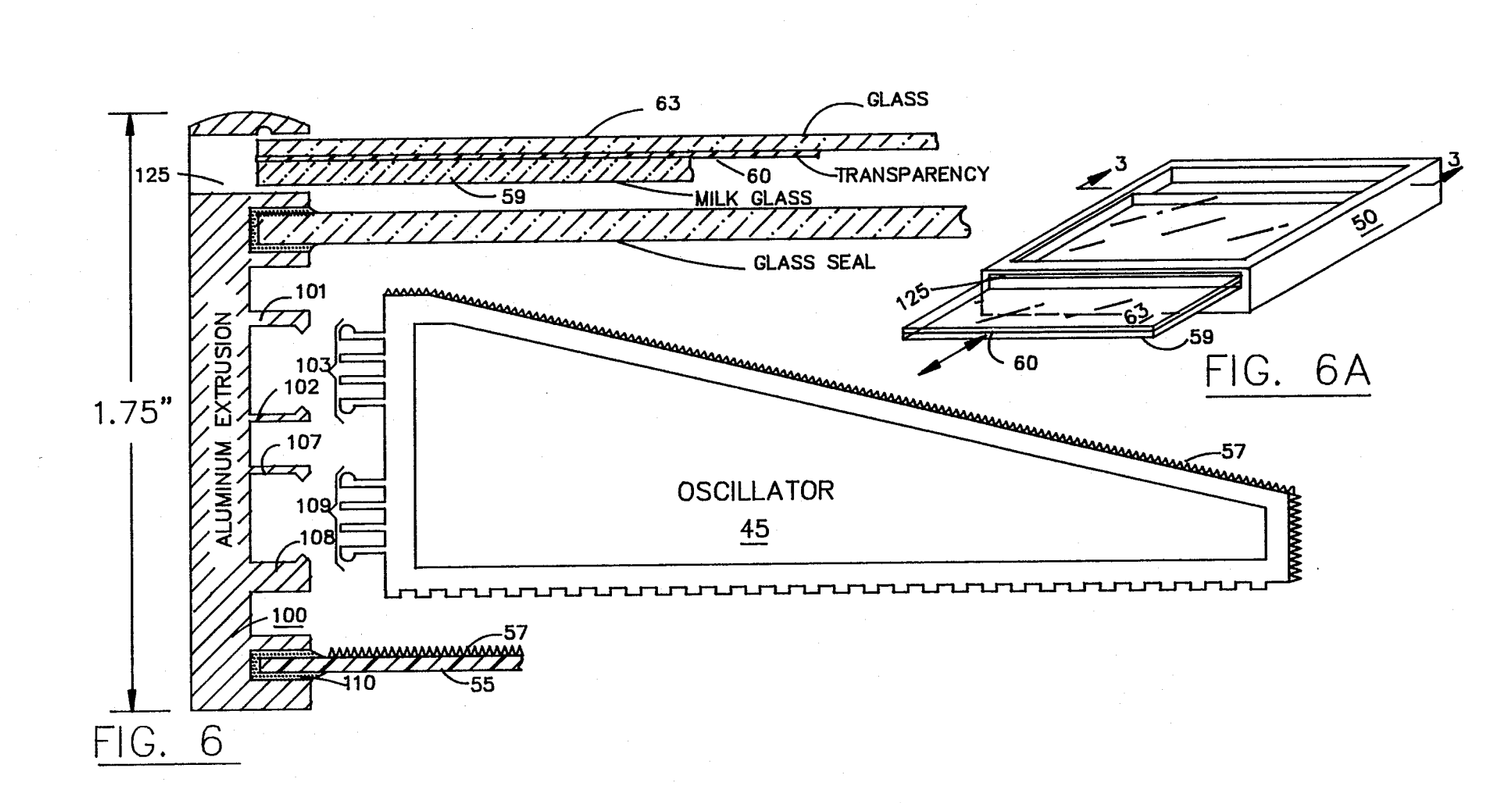
FIG. 6 is a section through a portion of the box to show interior structure thereof and the contained high frequency ballast circuit.
FIG. 6A shows the box housing with transparency and supporting structure therefor being slid out of the box.

In FIG. 3, a structure for one type of box or housing 50 of FIG. 6A is shown in cross section to reveal both direct and reflected light paths for lighting source 15 to support 51.

When the transparency is directly supported by glass seal 51, as in thin wall pictures (see FIG. 11) a glossy milk back acrylic is coated on the underneath side to serve as a diffuser, and the extrusion 100 (FIG. 6) is foreshortened to eliminate provision for glass 59, transparency 60 and top glass 63.

The bottom 55 of box 50 of either embodiment is sectioned for plastic, but may be any suitable, preferably light weight material, particularly if the box is to be incorporated into a hanging wall picture or display. The interior of bottom 55 is coated with a matte or crinkle coating 57, such as hair cell ABS, to attain uniform illumination (due to reflected light) at transparency 60, whether on glass 51 or on high transmission type milk glass diffusser 59 (FIG. 1).

The combination of short gap between bottom 55 and glass 51 or glass 59, complicated by both direct and indirect light, renders such a coating necessary. For example, aluminum foil, with or without patterning, solid white, gold, gold anodized or mirror will not permit high brilliancy uniform illumination. As a matter of fact, a mirror finish on bottom 55 blocks 60% of the light which should reach transparency 60. The matte or crinkle-like coating 57 is preferably patterned with a "leather" look for optimum performance.

It is the combination of the coating 57 and a light diffuser, such as milk glass 59 or a diffuser coating on the lower side of transparency 60 (FIG. 6) or acrylic diffuser coating on the bottom of glass seal 51 (FIG. 3) which resolves the short 1 to 1½ inch gap problem.

The uniform brilliancy at the front glass 63 gives the impression of an aura or glow so that a picture of the Mona Lisa becomes exceptionally alluring.

Returning to FIG. 3, direct light rays are illustrated at 65, 67, 69 and 71, for example, whereas reflected rays are shown at 73, 75, 77 and 79. All rays result in transmitted light passing through glass seal 51 (or milk glass 59 in FIG. 6) because the interior walls and components, such as 45 (FIG. 6) may be coated, as shown at 57 on high frequency ballast circuit 45 (FIG. 6) and bottom 55. Of course, the rays shown are but a tiny fraction of the light used.

The neon bulb 15 (FIG. 3) is supported by shock absorbing RTV glue mounds 80, 81 in turn carried by bottom 55. This is a transparent cement commercially available.

Figure 4:
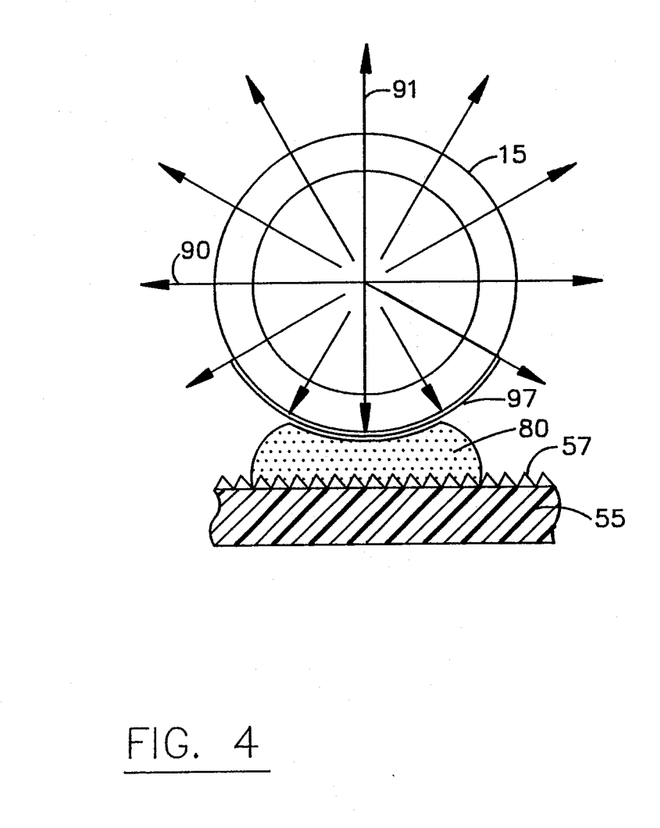
FIG. 4 shows a section through a neon tube to indicate direct emanating light therefrom.
Figure 5:
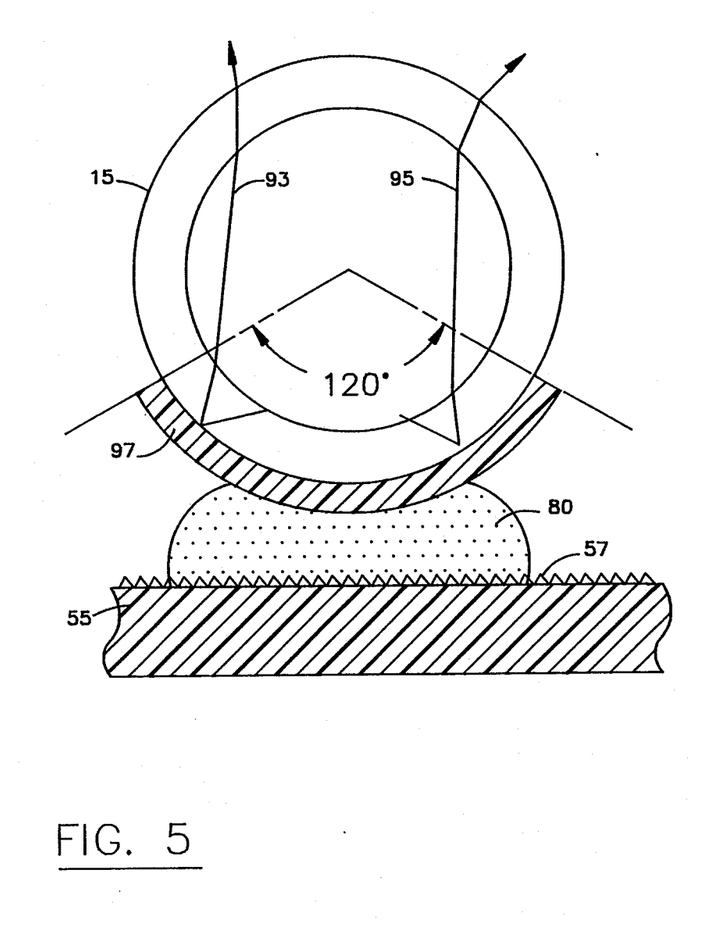
FIG. 5 reveals the structure of FIG. 4, in greater detail, to show indirect light emanating therefrom.

FIGS. 4 and 5 show the bulb 15, mounting 80 therefor and light emanations in greater detail. In FIG. 4, only the direct rays, such as 90, 91 are shown, whereas FIG. 5 shows internally reflected rays 93, 95 due to exterior coating 97 on approximately the lower one third or 120 degrees of tube 15. Coating 97 may simply comprise glass paint, preferably white in color, and is applied by dipping the light source 15 (FIG. 1) into a pan of paint. In this manner, maximum light from the source 15 is useful.

In FIGS. 6 and 6A, it will be seen that the box 50 sides and ends may comprise aluminum extrusions 100 having a height of 1.75 inches.

The tines 101 and 102 are adapted to receive and grip high frequency ballast circuit 45 tines 103, while tines 107 and 108 receive tines 109. This structure suspends the high frequency ballast circuit 45 from extrusion 100, and it can be located at any position across the box 50. Also, coating 57 eliminates any shadow which high frequency ballast circuit 45 might cause if not located under a border.

Bottom 50 is glued into extrusion 100 as shown at 110 to prevent airbornes and bugs from entering the box. Similarly, glass seal 51 is glued to extrusion 100 at 111.

The transparency 60 is sandwiched between milk glass support 59 and glass top 63 for sliding movement into and out of box 50 via slot 125 to permit changing of the transparency images. Slot 125 provides a tight fit and the glass sandwich protects the image.

Figures 7, 7A, 8, 9:
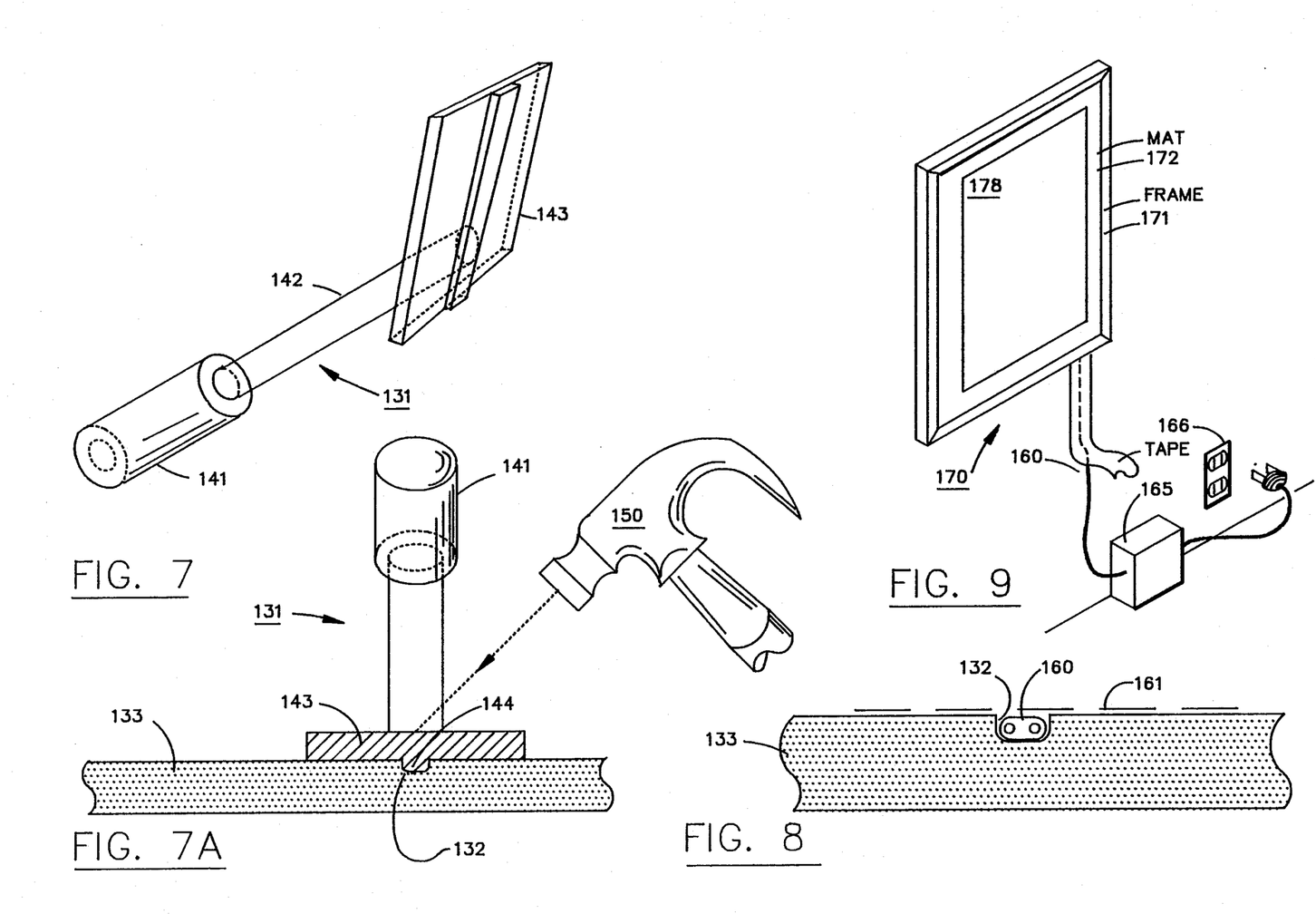
FIG. 7 is a view of a grooving tool for drywall.
FIG. 7A shows the grooving tool in operative engagement with a drywall.
FIG. 8 shows an electrical cord embedded in the drywall.
FIG. 9 shows a portrait picture on a wall with tape for obscuring the cord.

FIGS. 7 and 7A show a tool 131 for forming groove 132 (FIGS. 7A and 8) in drywall 133. Tool 131 comprises a handle 141, shaft 142, platform 143 and grooving element 144. Hammer 150 is used to tap platform 143 and drive grooving element 144 into drywall 133. Strangely enough, the drywall does not crack but permits formation of a perfect groove 132. This enables hiding of electrical cord 160 in groove 132 by tape 161. The tape may match the color of the wall or it may be painted.

Picture 170 (FIG. 9) includes frame 171 and mat border 172 with cord 160 extending to TR set 165 for plug-in to a wall socket 166. The image or portrait 178 replaces the box glass top 63, transparency 60 and milk glass 59. A different extrusion from extrusion 100 is used to permit glass seal 51 to bear against a diffuser surface, in turn in contact with portrait 178. A plastic sheet high transmissive diffuser may be used or glass seal 51 may simply comprise milk glass or a milk glass type coating.

Figure 10:
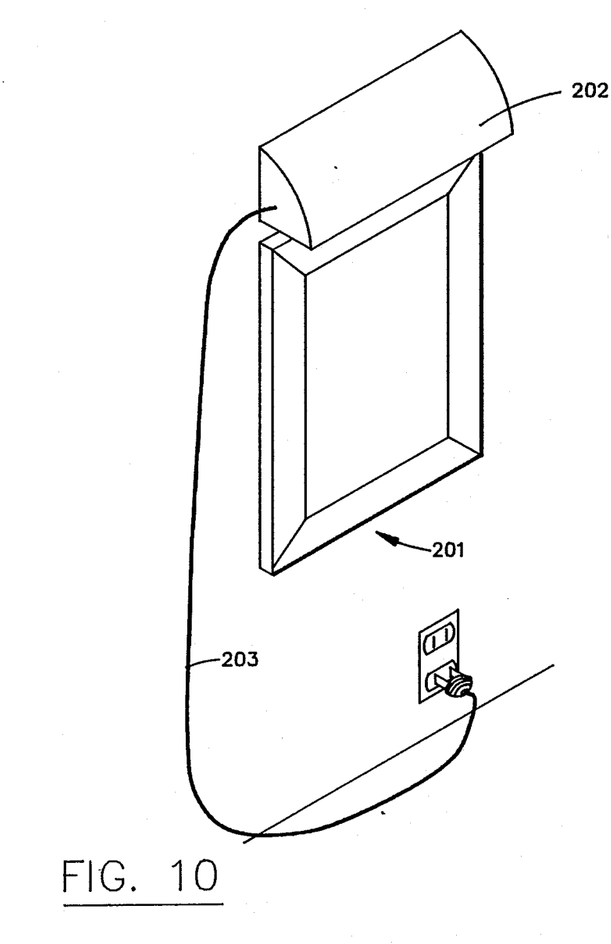
FIG. 10 illustrates a conventionally displayed wall picture.
Figure 11:
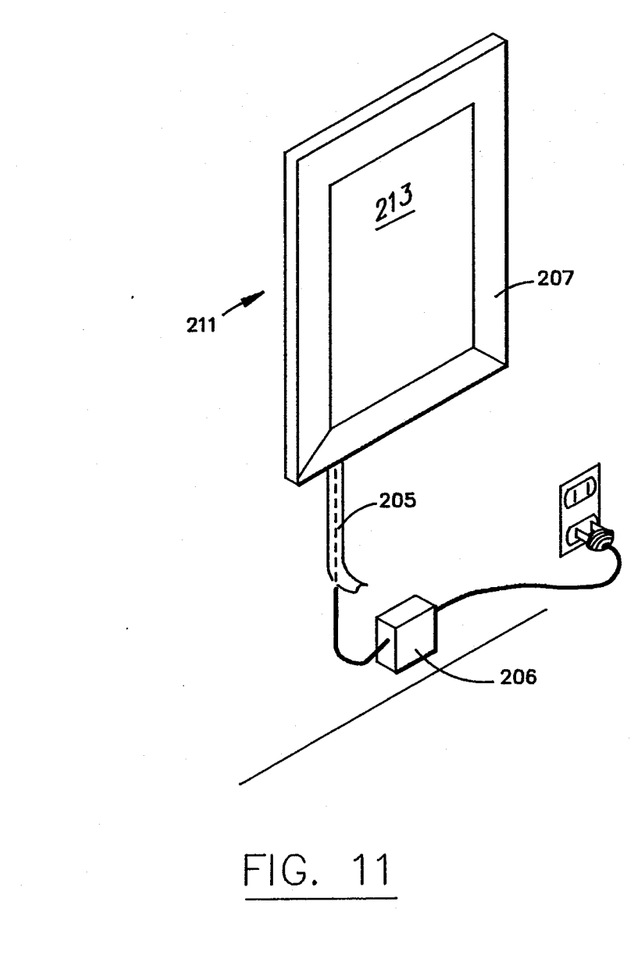
FIG. 11 shows a thin, wall supported, self-illuminated picture using principles of the present invention.

FIGS. 10 and 11 show respectively a prior art method of illuminating picture 201, in contrast to a self-illuminating picture 211. The expensive light 202 in FIG. 10 is usually installed by an electrician at additional cost. Here, however it is pictured with undesirable cord 203 exposed.

In FIG. 11, the cord 205 is hidden and only TR set 206 is exposed. Also, border 207 permits hiding of the high frequency ballast circuit. Picture 211 is of the thin type using a box having a depth of less than 2 inches with image or portrait 213 having a diffuser rear coating and being against glass seal 51 (FIG. 6). Alternatively, glass seal 51 may comprise milk glass and replace the diffuser. The box 50 is simply fastened to frame 207, as by screws, not shown, and the bottom of the box may have a stick-on surface or a "velcro" cover to hang directly on the wall.

Figure 12:
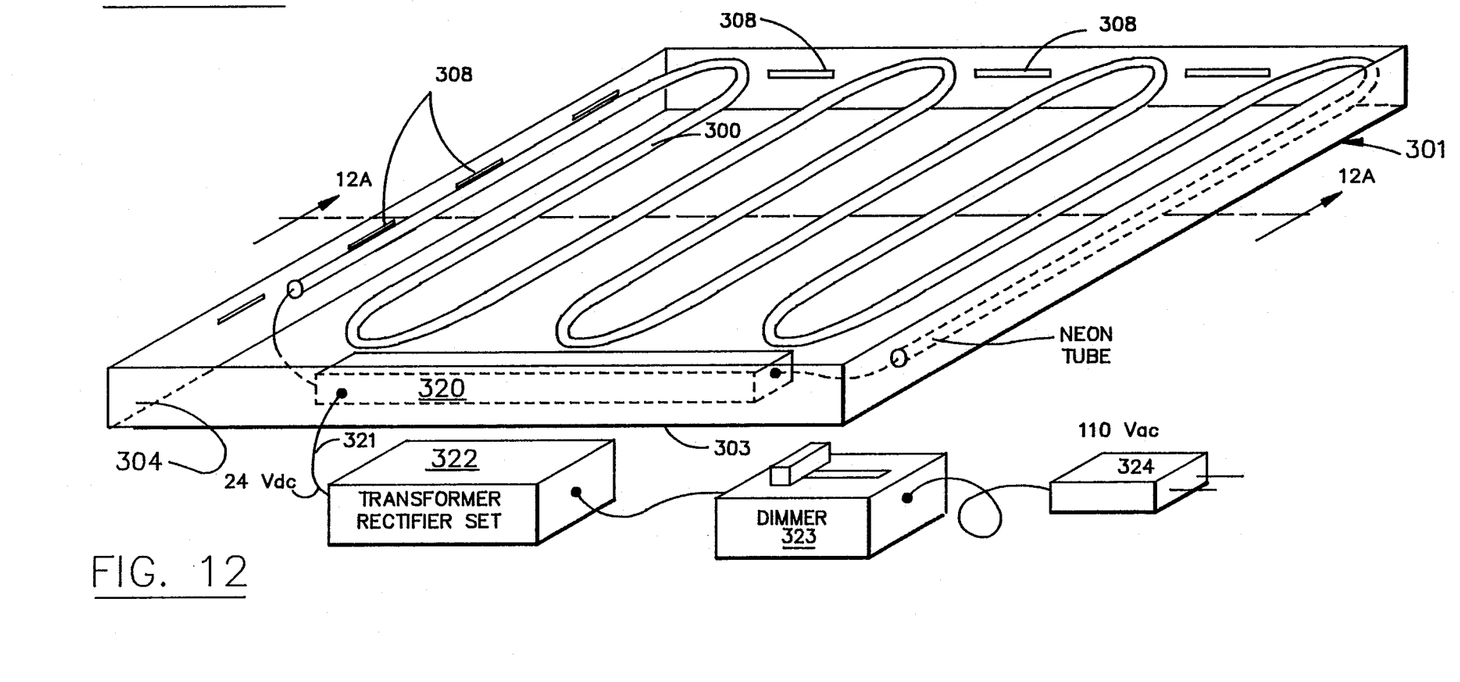
FIG. 12 shows a combination light box and transparency.
Figure 12A:
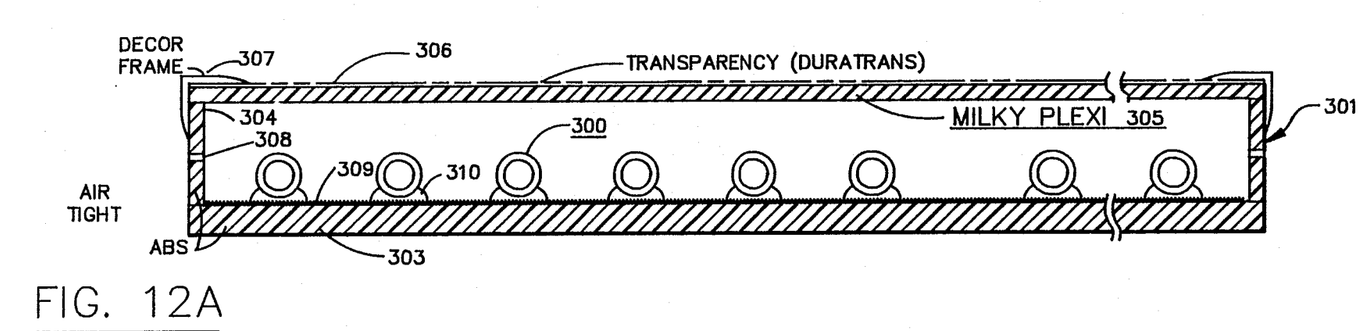
FIG. 12A is a sectional view, taken along the plane 12A—12A of FIG. 12.

In FIG. 12 there is depicted a light box picture frame combination 301 which is preferably constructed of ABS plastic bottom 303, sides 304 and includes a milky plexi top window 305—all glued together in air-tight configuration.

Inside box 301 is the neon lighting source 300, supported by glue mounds 310 above the matte coating 309, and the high frequency ballast circuit 320. Note that the hight frequency ballast circuit 320 may be obscured by decor frame 307 being located along an inner edge of the box 301 (or it may be coated by coating 309 to avoid casting a shadow).

High frequency ballastic circuit 320 is connected over lead 321 (through a sealed connector, not shown) to a transformer rectifier set or conventional power supply 322, in turn connected to dimmer 323 supplied with 110 Vac via electrical plug 324. Dimmer 323 is a commercial product, available from Gemini, Center Valley, PA for $3.50.

The frame 307 is glued to plastic box 301 leaving a peripheral space for transparency 306. This construction provides a dust-free display.

A halo effect is generated by slots 308 permitting light to emanate about the periphery of transparency 306.

In summary, the light box of the present invention is less than 50% of the thickness of conventional light boxes, and weighs only about 20% thereof. Even the light provides a new effect as it has a uniform brilliance of 3 to 4% even at 100 lumens. The use of a slant surface which is crinkle coated as the exposed surface of the high frequency ballast circuit serves to light the area of the high frequency ballast circuit. Slant-mounting the high frequency ballast circuit is an alternative to a slant surface therefor.

The use of a plastic bottom for the box prevents load-up of the neon bulb. The hair cell finish is a glossy acrylic and provides the right amount of reflection for the small gap.

The well-known Dura Transparency has a built-in or integral diffuser, whereas the advantage of a Ciba Transparency is its stability to withstand ultra-violet light—this polyester resin based film being stable for 500 years.

The exciting high frequency for the neon or cathode light optimizes detail better than conventionally excited neon bulbs in conventional arrangements.

By incorporating a battery charge kit, a portable sign, display, or picture may be obtained—even built into a small or medium sized suitcase.

It has been found that the paint coating 97 for the lower portion of neon tube 15 in FIG. 5 should preferably be white for the device herein detailed.

The subject light box has been found to be suitable to high resolution in computer graphic use.

In general, uses for the equipment herein described fall into five major categories; namely, Decorative Art, Signs, Light Boxes, Home, and Commercial Buildings. Decorative Art encompasses hotels, restaurants, offices and architects (for renderings). Signs cover particularly the Beer Industry, Point of Sales, and Outdoor signs. Light Boxes include Photographers, Art Directors, Cartographers, Circuit Board Configuring, and Drafting. Home uses include Wall Pictures; and, Commercial Buildings may use the invention as whole ceilings (also Home Use) and as Light Sources. The costs for maintenance and electrical services are absolutely minimal.

The oscillators are available from:
AVE MICROSYSTEMS or INTELITE INC.
625 W. KATELLA AVENUE
ORANGE, CA 92667

What is claimed is:

1. A thin cool light display, comprising in combination:
   a box having a depth of the order of 2 inches or less from bottom to top;
   a window in the top of the box;
   elongated cold cathode lighting means configured to fit within the box and extend substantially entirely across the bottom thereof and supported within the box adjacent to the bottom of the box;
   a transparency adjacent to the window; one of a diffusing coating on the back of the transparency or a diffuser element adjacent to the back of the transparency;
   a high frequency ballast circuit within the box adapted to supply high frequency energy to the lighting means;
   means external to the box for supplying power to the oscillator;
   a crinkle coating in the box at least on the bottom thereof to enable substantially uniform and continuous brightness to emanate from the window.

2. The display of claim 1, wherein:
   said coating substantially covers the the high frequency ballast circuit for light reflection therefrom.

3. The display of claim 1, wherein:
   the cold cathode lighting means comprise a neon tube configured to extend substantially across and lengthwise of said bottom to provide substantially uniform brilliance at said window.

4. The display of claim 1, further comprising:
   a transformer-rectifier set remote from the display and connected thereto to supply low voltage dc power to the oscillator.

5. The display of claim 1, further comprising:
   a transformer remote from the display, and connected thereto to supply low voltage ac power from rectification by a rectifier for application to said oscillator.

6. The display of claim 1 further comprising:
   a reflective coating on the exterior of the neon tube adjacent to the bottom of the box to reflect light toward the window.

7. The display of claim 1, further comprising:
   a frame for said transparency connected to said box to form a picture suitable for wall hanging.

8. The display of claim 7, further comprising:
   means external to said box for supplying power to a transformer;
   said means comprising an electrical cord embedded in the wall.

9. The display of claim 8, wherein:
   said means external further comprising:
   means for supplying low voltage to said rectifier via said cord.

10. The method of displaying an image, comprising the steps of:
    coating at least a substantial part of the interior of a box with a light reflecting matte finish;
    disposing an elongated cold cathode light source adjacent the bottom of the box configured to fit within the box, and to extend across the bottom of the box to direct light upwardly through the top of the box directly and reflectively; making the thickness of the box less than 2 inches; disposing a pane in the top of the box to seal it; placing a transparency adjacent the pane outside of the box; and, supplying high frequency, low current power from a high frequency ballast circuit located within the box to the light source to provide direct and reflected light at said transparency of substantially uniform brilliance.

* * * * *